US010875889B2

(12) United States Patent
Jakel

(10) Patent No.: US 10,875,889 B2
(45) Date of Patent: Dec. 29, 2020

(54) METHOD AND SYSTEM FOR PRODUCING A ZEIN PROTEIN PRODUCT FROM A WHOLE STILLAGE BYPRODUCT PRODUCED IN A CORN DRY-MILLING PROCESS

(71) Applicant: Fluid Quip Technologies, LLC, Springfield, OH (US)

(72) Inventor: Neal Jakel, Cedar Rapids, IA (US)

(73) Assignee: Fluid Quip Technologies, LLC, Springfield, OH (US)

( * ) Notice: Subject to any disclaimer, the term of this patent is extended or adjusted under 35 U.S.C. 154(b) by 0 days.

(21) Appl. No.: 16/235,363

(22) Filed: Dec. 28, 2018

(65) Prior Publication Data

US 2020/0207807 A1    Jul. 2, 2020

(51) Int. Cl.
| | | |
|---|---|---|
| *C07K 1/36* | (2006.01) | |
| *B01D 3/14* | (2006.01) | |
| *B01D 11/04* | (2006.01) | |
| *B01D 21/26* | (2006.01) | |
| *C07K 14/425* | (2006.01) | |

(52) U.S. Cl.
CPC ............... *C07K 1/36* (2013.01); *B01D 3/148* (2013.01); *B01D 11/0492* (2013.01); *B01D 21/262* (2013.01); *B01D 21/267* (2013.01); *C07K 14/425* (2013.01)

(58) Field of Classification Search
CPC ....................................................... C07K 1/36
See application file for complete search history.

(56) References Cited

U.S. PATENT DOCUMENTS

| | | | |
|---|---|---|---|
| 4,361,651 A | 11/1982 | Keim | |
| 4,624,805 A | 11/1986 | Lawhon | |
| 5,066,498 A | 11/1991 | McCauley, III | |
| 5,177,008 A | 1/1993 | Kampen | |
| 5,250,182 A | 10/1993 | Bento et al. | |
| 5,662,810 A | 9/1997 | Willgohs | |
| 5,958,233 A | 9/1999 | Willgohs | |
| 6,071,378 A | 6/2000 | Saito | |
| 6,095,065 A | 8/2000 | Dietrich, Sr. | |
| 6,433,146 B1 * | 8/2002 | Cheryan ................. A23J 1/142 530/370 |
| 6,509,180 B1 | 1/2003 | Verser et al. | |
| 6,962,722 B2 | 11/2005 | Dawley et al. | |
| 7,101,691 B2 | 9/2006 | Kinley et al. | |
| 7,351,559 B2 | 4/2008 | Verser et al. | |
| 7,494,675 B2 | 2/2009 | Abbas et al. | |
| 7,601,858 B2 | 10/2009 | Cantrell et al. | |
| 7,608,729 B2 | 10/2009 | Winsness et al. | |
| 7,829,680 B1 | 11/2010 | Sander et al. | |
| 8,008,516 B2 | 8/2011 | Cantrell et al. | |
| 8,008,517 B2 | 8/2011 | Cantrell et al. | |
| 8,103,385 B2 | 1/2012 | Macharia et al. | |
| 8,168,037 B2 | 5/2012 | Winsness | |
| 8,257,951 B2 | 9/2012 | Prevost et al. | |
| 8,283,484 B2 | 10/2012 | Cantrell et al. | |
| 8,679,353 B2 | 3/2014 | Winsness | |
| 8,679,793 B2 | 3/2014 | Lewis | |
| 8,722,911 B2 | 5/2014 | Bleyer et al. | |
| 8,778,433 B2 | 7/2014 | Lee | |
| 8,813,973 B2 | 8/2014 | Lee et al. | |
| 8,906,204 B2 | 12/2014 | Xu | |
| 8,956,460 B2 | 2/2015 | Ahmed et al. | |
| 8,986,551 B2 | 3/2015 | Kohl et al. | |
| 9,029,126 B2 | 5/2015 | Bleyer et al. | |
| 9,066,531 B2 | 6/2015 | Williams | |
| 2003/0180415 A1 | 9/2003 | Stiefel et al. | |
| 2004/0082044 A1 | 4/2004 | Prevost et al. | |
| 2004/0087808 A1 | 5/2004 | Prevost et al. | |
| 2006/0006116 A1 | 1/2006 | Scheimann et al. | |
| 2006/0040024 A1 | 2/2006 | Srinivasan et al. | |

(Continued)

FOREIGN PATENT DOCUMENTS

| | | |
|---|---|---|
| CN | 1242879 C | 2/2006 |
| EP | 0395556 A1 | 10/1990 |

(Continued)

OTHER PUBLICATIONS

Wolf et al. Cereal Chem. 1997, 74(5):530-536.*
Xu et al. J Agric Food Chem. 2007, 55:6279-6284.*
Shuka, Rishi et al, Zein: The Industrial Protein from Corn, Agricultural Bioprocess Laboratory, University of Illinois at Urbana-Champaign, Jan. 28, 2000.
Zhang et al, "DDGS Production Technology, Research and Utilization Satus and Application in Livestock and Poultry Production," Animals Breeding and Feed, Issue 10, pp. 38-42 (5 pages).

(Continued)

*Primary Examiner* — Bin Shen

(74) *Attorney, Agent, or Firm* — Wood Herron & Evans LLP

(57) ABSTRACT

A method and system are disclosed for producing a zein protein product from a whole stillage byproduct produced in a corn (or similar carbohydrate-containing grain) dry-milling process for making alcohol, such as ethanol, and/or other biofuels/biochemicals. In one embodiment, the method includes separating the whole stillage byproduct into an insoluble solids portion and a centrate (solubles) portion, which includes protein, such as zein protein. Thereafter, the centrate (solubles) portion can be separated into a water soluble solids portion and a protein portion, which includes zein protein. Zein protein may be separated out from the protein portion. The remaining protein portion may be further processed to produce a high protein corn meal. The resulting zein protein portion may be further processed to be sold as a zein protein product and/or used as or in, for example, coatings, fibers, adhesives, ceramics, inks, cosmetics, textiles, food products, pharmaceutical, and biodegradable plastics.

19 Claims, 4 Drawing Sheets

(56) References Cited

U.S. PATENT DOCUMENTS

| | | |
|---|---|---|
| 2006/0041153 A1 | 2/2006 | Cantrell et al. |
| 2006/0057251 A1 | 3/2006 | Dawley et al. |
| 2006/0071378 A1 | 4/2006 | Brown |
| 2006/0091050 A1 | 5/2006 | Hwang |
| 2006/0173169 A1 | 8/2006 | Cheryan |
| 2006/0194296 A1 | 8/2006 | Hammond et al. |
| 2007/0039853 A1 | 2/2007 | Angulo Aramburu |
| 2007/0254089 A1 | 11/2007 | Hickey et al. |
| 2008/0026101 A1 | 1/2008 | Nickel et al. |
| 2008/0044547 A1 | 2/2008 | DeLine et al. |
| 2008/0095890 A1 | 4/2008 | Watson |
| 2008/0110577 A1 | 5/2008 | Winsness |
| 2008/0299632 A1 | 12/2008 | Winsness et al. |
| 2009/0029432 A1 | 1/2009 | Abbas et al. |
| 2009/0130257 A1 | 5/2009 | Abbas et al. |
| 2009/0250412 A1 | 10/2009 | Winsness et al. |
| 2009/0259060 A1 | 10/2009 | Cantrell et al. |
| 2010/0004474 A1 | 1/2010 | Cantrell et al. |
| 2010/0260918 A1 | 10/2010 | Wang et al. |
| 2011/0143013 A1* | 6/2011 | Lawton, Jr. .......... C07K 14/425 426/656 |
| 2012/0121565 A1 | 5/2012 | Williams |
| 2012/0205324 A1 | 8/2012 | Cantrell et al. |
| 2012/0312905 A1 | 12/2012 | Claycamp |
| 2013/0164795 A1 | 6/2013 | Lowe et al. |
| 2014/0053829 A1 | 2/2014 | Lee |
| 2014/0142282 A1 | 5/2014 | Emanuele et al. |
| 2014/0147897 A1 | 5/2014 | Lee |
| 2014/0212543 A1 | 7/2014 | Lywood et al. |
| 2014/0220650 A1 | 8/2014 | Woods et al. |
| 2014/0242251 A1 | 8/2014 | Bootsma |
| 2014/0319066 A1 | 10/2014 | LoCascio et al. |
| 2014/0343259 A1 | 11/2014 | Bleyer et al. |
| 2015/0010975 A1 | 1/2015 | Burlew et al. |
| 2015/0056327 A1 | 2/2015 | Redford |
| 2015/0060259 A1 | 3/2015 | Xu |
| 2015/0064308 A1 | 3/2015 | Williams |
| 2015/0068058 A1 | 3/2015 | Buettner et al. |
| 2015/0080203 A1 | 3/2015 | Martyniuk |
| 2017/0166835 A1 | 6/2017 | Jakel |

FOREIGN PATENT DOCUMENTS

| | | |
|---|---|---|
| EP | 0636692 A1 | 2/1995 |
| EP | 1988169 A1 | 11/2008 |
| WO | 8606098 A1 | 10/1986 |
| WO | 2010109203 A1 | 9/2010 |
| WO | 201414683 A1 | 1/2014 |
| WO | 2014014682 A1 | 1/2014 |
| WO | 201426947 A1 | 2/2014 |
| WO | 201433476 A2 | 3/2014 |
| WO | 2016123258 A1 | 8/2016 |

OTHER PUBLICATIONS

Lawton, John W., "Zein: A history of processing and use", Cereal Chemi, ACC International Inc, US, vol. 79, No. 1, Jan. 1, 2002, pp. 1-18.

European Patent Office, Extended Search Report issued in EP 19153885.9 dated Aug. 19, 2019, 7 pages.

\* cited by examiner

METHOD AND SYSTEM FOR PRODUCING A ZEIN PROTEIN PRODUCT FROM A WHOLE STILLAGE BYPRODUCT PRODUCED IN A CORN DRY-MILLING PROCESS

TECHNICAL FIELD

The present invention relates generally to corn dry-milling, and more specifically, to a method and system for producing a zein protein product from a whole stillage byproduct produced in a corn (or similar carbohydrate-containing grain) dry-milling process for making alcohol, such as ethanol, and/or other biofuels/biochemicals.

BACKGROUND

Wet mill processing plants convert, for example, corn grain, into several different co-products, such as germ (for oil extraction), gluten feed (high fiber animal feed), gluten meal (high protein animal feed) and starch-based products such as alcohol (e.g., ethanol or butanol), high fructose corn syrup, or food and industrial starch. However, because constructing wet-milling plants is complex and capital-intensive, almost all new plants built today are dry-milling plants.

Dry milling plants generally convert grains, such as corn, into three products, namely alcohol (e.g., ethanol or butanol), distillers corn oil, and distiller's grains with solubles. A typical corn dry-milling process consists of four major steps: grain handling and milling, liquefaction, saccharification and fermentation, and co-product recovery. Grain handling and milling is the step in which the corn is brought into the plant and ground to promote better starch to glucose conversion. Liquefaction and saccharification is where the starch is converted into glucose. Fermentation is the process of yeast converting glucose into alcohol. Co-product recovery is the step in which the alcohol (e.g., ethanol) and corn by-products are purified and made market ready.

The recovery of alcohol (e.g., butanol, ethanol, etc.) and natural co-products generally begins with the beer (spent fermentation broth) being sent to a distillation system. With distillation, ethanol is typically separated from the rest of the beer through a set of stepwise vaporizations and condensations. The beer less the alcohol extracted through distillation is known as whole stillage, which contains a slurry of the spent grains including corn protein, fiber, oil, minerals, and sugars as well as spent yeast. These byproducts are too diluted to be of much value as mixed together at this point and are further processed to provide the distiller's grains with soluble.

In typical processing, when the whole stillage leaves the distillation column, it is generally subjected to a decanter centrifuge to separate insoluble solids or "wet cake", which includes mostly fiber, from the liquid or "thin stillage", which includes, e.g., protein, oil, and amino acids. After separation, the thin stillage moves to evaporators to boil away moisture, leaving a thick syrup that contains soluble (dissolved) solids. The concentrated syrup is typically mixed with the wet cake, and the mixture may be sold to beef and dairy feedlots as distillers wet grain with solubles (DWGS). Alternatively, the wet cake and concentrated syrup mixture may be dried in a drying process and sold as distillers dried grain with solubles (DDGS). The resulting DDGS generally has a crude protein content of about 29% and is a useful feed for cattle and other ruminants due to its protein and fiber content. The resulting product is a natural product.

While DDGS and DWGS provide a critical secondary revenue stream that offsets a portion of the overall ethanol production cost, it would be beneficial to provide a method and system where a back end stream(s) in the corn dry-milling process can be utilized to recover one or more other products that can provide other or additional revenue sources.

SUMMARY

The present invention relates to a method and system for producing a zein protein product from a whole stillage byproduct produced in a corn dry-milling process for making alcohol, such as ethanol, and other biofuels/biochemicals.

In one embodiment, a method for producing a zein protein product from a whole stillage byproduct is disclosed that includes separating a whole stillage byproduct into an insoluble solids portion and a solubles portion, which includes zein protein. Then, prior to any evaporation step, the solubles portion is separated into a protein portion including the zein protein, and a water soluble solids portion. In one example, the solubles portion is separated, via weights, into a protein portion including the zein protein, and a water soluble solids portion. The zein protein is next separated from the protein portion to define a zein protein portion and a remaining protein portion, and then the zein protein portion is recovered to define a zein protein product, which includes at least 30 wt % zein protein on a dry basis.

In another embodiment, a method for producing a zein protein product from a whole stillage byproduct is discloses that includes separating a whole stillage byproduct into an insoluble solids portion and a solubles portion, which includes zein protein. Then, prior to any evaporation step, the solubles portion is separated into a protein portion including the zein protein, and a water soluble solids portion. In one example, the solubles portion is separated, via weights, into a protein portion including the zein protein, and a water soluble solids portion. The zein protein is next extracted from the protein portion, then the extracted zein protein separated from the protein portion to define a zein protein portion and a remaining protein portion. Thereafter, the zein protein portion is precipitated out or solvent removed from the zein protein portion to define a zein protein product, which includes at least 30 wt % zein protein on a dry basis.

In another embodiment, a system for producing a zein protein product from a whole stillage byproduct is disclosed that includes a first apparatus that is situated after a distillation column for distilling alcohol and that receives a whole stillage byproduct, the first apparatus separates the whole stillage byproduct into an insoluble solids portion and a solubles portion, which includes zein protein. A second apparatus is situated after the first apparatus and prior to any evaporator and receives the solubles portion from the first apparatus, wherein the second apparatus separates the solubles portion into a protein portion, including the zein protein, and a water soluble solids portion. In one example, the second apparatus separates the solubles portion, via weights, into a protein portion, including the zein protein, and a water soluble solids portion. An evaporator situated after the second apparatus and receives the water soluble solids portion but does not receive the solubles portion, wherein the evaporator separates soluble solids from the water soluble solids portion, via evaporation. A zein protein extraction system is situated after the second apparatus and extracts the zein protein from the protein portion, which is received from the second apparatus. A third apparatus is situated after the extraction system and separates the extracted zein protein from the protein portion, which is received from the extraction system, to define a zein protein portion and a remaining protein portion. And a recovery system is situated after the third apparatus and recovers the separated zein protein portion to define a zein protein product, which includes at least 30 wt % zein protein on a dry basis.

Zein, an alcohol-soluble storage protein, comprises 45-50% of the protein in corn. Almost all of the zein is present in the endosperm. Zein is rich in glutamic acid, leucine, proline, and alanine but is deficient in basic and acidic amino acids. Zein and its resins can form tough, glossy, hydrophobic grease-proof coatings that are resistant to microbial attack. Other applications of zein include, but are not limited to, use in fibers, adhesives, ceramics, inks, cosmetics, textiles, food products, pharmaceuticals, and biodegradable plastics.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

The present invention is directed to a method and system for producing a zein protein product from a whole stillage byproduct produced in a corn dry-milling process for making a biofuel, e.g., ethanol, or a biochemical, e.g., lactic acid.

Figure 1:
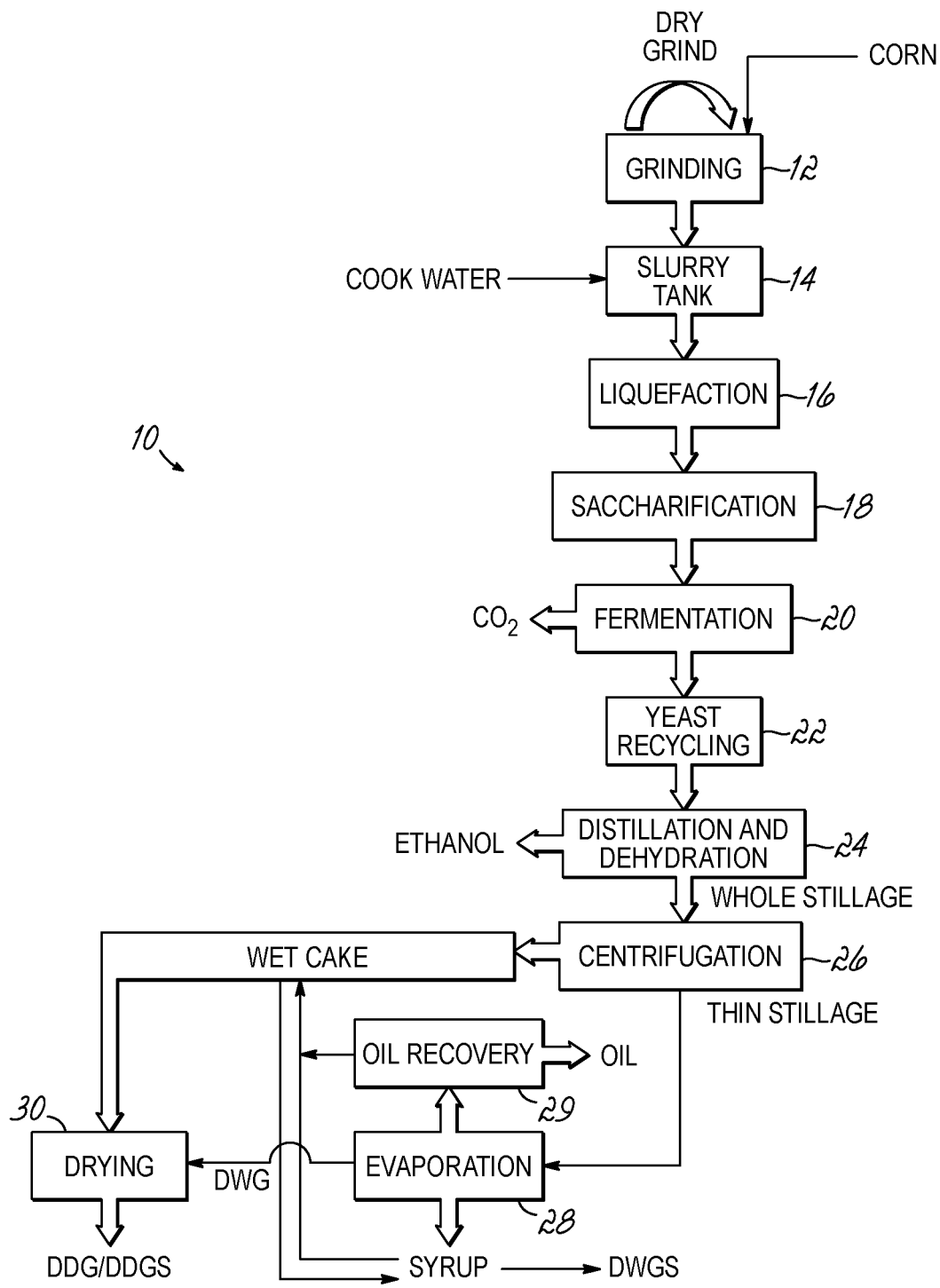
FIG. 1 is a flow diagram of a prior art dry-milling process and system for producing ethanol and distiller's grains with solubles.

FIG. 1 is a flow diagram of a prior art corn dry milling process for producing alcohol, such process is fully discussed in U.S. Pat. No. 8,778,433, entitled "Methods for producing a high protein corn meal from a whole stillage byproduct". A significant portion of alcohol, e.g., ethanol, in the United States is produced from dry milling processes, which convert corn into two products, namely ethanol and distiller's grains with solubles. Although virtually any type and quality of grain, such as but not limited to sorghum, wheat, triticale, barley, rye, tapioca, cassava, potato, and other starch containing grains can be used to produce ethanol, the feedstock for this process is typically corn referred to as "No. 2 Yellow Dent Corn."

With specific reference to FIG. 1, a typical corn dry-milling process 10 begins with a grinding step 12 in which dried whole corn kernels are passed through hammer mills to grind them into meal or a powder. After the grinding step 12, the ground meal can be mixed with cook water to create a slurry at slurry step 14, and a commercial enzyme such as alpha-amylase is typically added (not shown). The slurry step 14 is followed by a liquefaction step 16 whereat the pH is adjusted to about 5.2 to about 5.8 and the temperature maintained between about 50° C. to about 105° C. so as to convert the insoluble starch in the slurry to soluble starch.

Liquefaction step 16 may be followed by followed by separate saccharification and fermentation steps, 18 and 20, respectively, although in most commercial dry grind ethanol processes, saccharification and fermentation can occur simultaneously. This single step is referred to in the industry as "Simultaneous Saccharification and Fermentation" (SSF). In the saccharification step 18, the liquefied mash is cooled and a commercial enzyme, such as gluco-amylase, is added to hydrolyze the maltodextrins and short-chained oligosaccharides into single glucose sugar molecules. In the fermentation step 20, a common strain of yeast (*Saccharomyces cerevisae*) is added to metabolize the glucose sugars into ethanol and $CO_2$. Other fermentation agents such as bacteria and clostridia can be utilized. Upon completion, the fermentation mash ("beer") will contain about 17% to 18% ethanol (volume/volume basis), plus soluble and insoluble solids from all the remaining grain components, including fiber, protein, minerals, and oil, for example. Yeast can optionally be recycled in a yeast recycling step 22. In some instances, the $CO_2$ is recovered and sold as a commodity product.

Subsequent to the fermentation step 20 is a distillation and dehydration step 24 in which the beer is pumped into distillation columns where it is boiled to vaporize the ethanol. The ethanol vapor is separated in the distillation columns, then condensed and liquid alcohol (in this instance, ethanol) exits the distillation columns at about 95% purity (190 proof). The 190 proof ethanol can then go through a molecular sieve dehydration column or a membrane separation unit or similar dehydration system, which removes the remaining residual water from the ethanol, to yield a final product of essentially 100% ethanol (199.5 proof).

Finally, a centrifugation step 26 involves centrifuging, via a decanter centrifuge, the residuals or whole stillage leftover from distillation so as to separate the insoluble solids portion or "wet cake", which includes fiber, from the liquid portion or "thin stillage" portion, which includes protein, amino acids, oil, etc. Next, the thin stillage portion enters evaporators in an evaporation step 28 in order to boil away moisture thereby leaving a thick syrup, which contains the soluble (dissolved) solids as well as protein and oil. The concentrated slurry can be sent to a centrifuge to separate the oil from the syrup in an oil recovery step 29. The oil can be sold as a separate high value product.

The resulting syrup is typically referred to as corn condensed distillers solubles and can be mixed with the centrifuged wet cake then sold to beef and dairy feedlots as distillers wet grain with solubles (DWGS). The wet cake and concentrated syrup mixture may be further dried in a drying step 30 and sold as distillers dried grain with solubles (DDGS) to dairy and beef feedlots and/or the monogastric markets. The distiller's grains with solubles co-product provides a critical secondary revenue stream that offsets a portion of the overall ethanol production cost.

Figure 2:
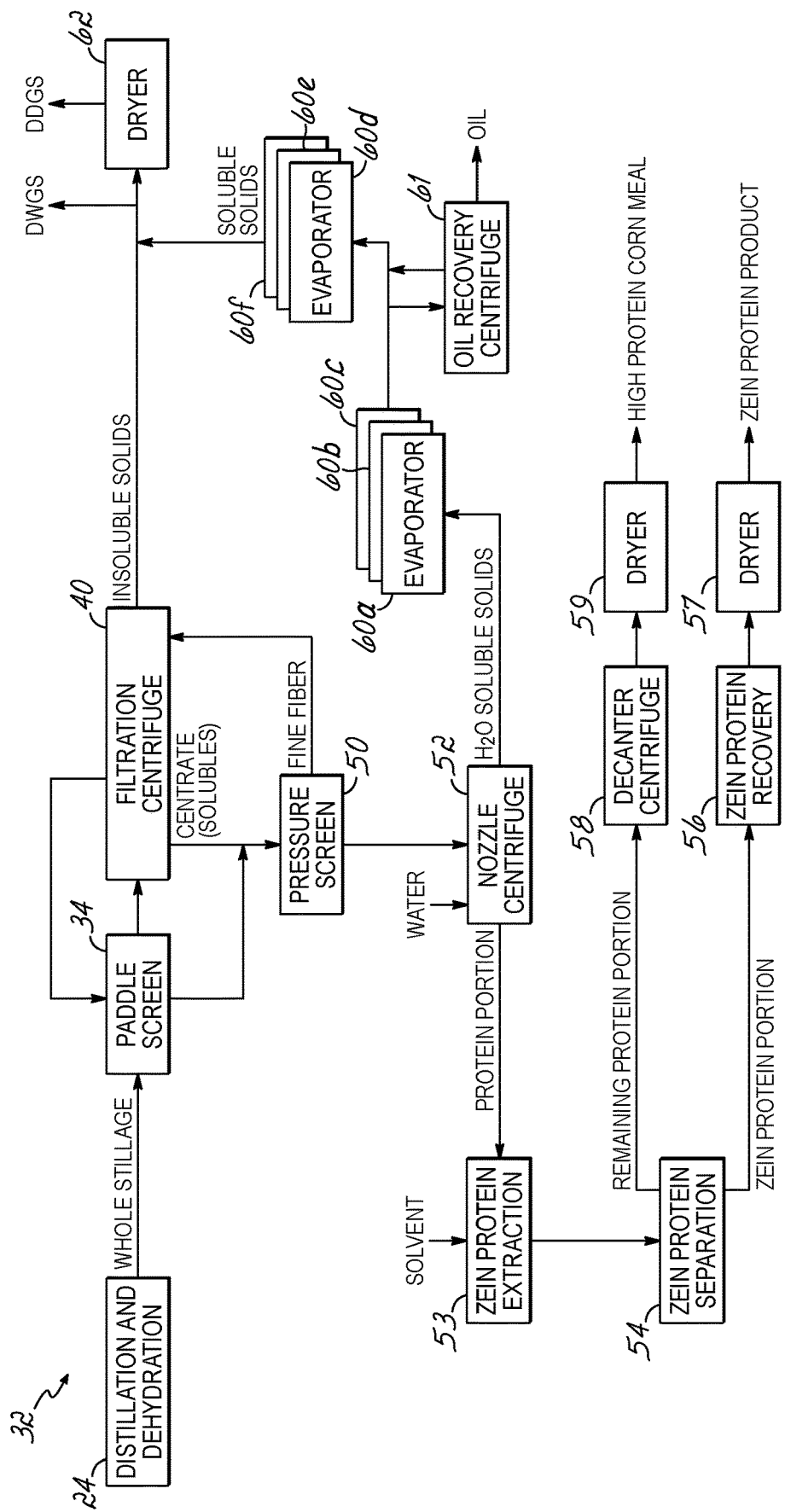
FIG. 2 is a flow diagram of a method and system for producing a zein protein product from a whole stillage byproduct produced via a corn dry-milling process for making alcohol (e.g., ethanol) in accordance with an embodiment of the invention.
Figure 2B:
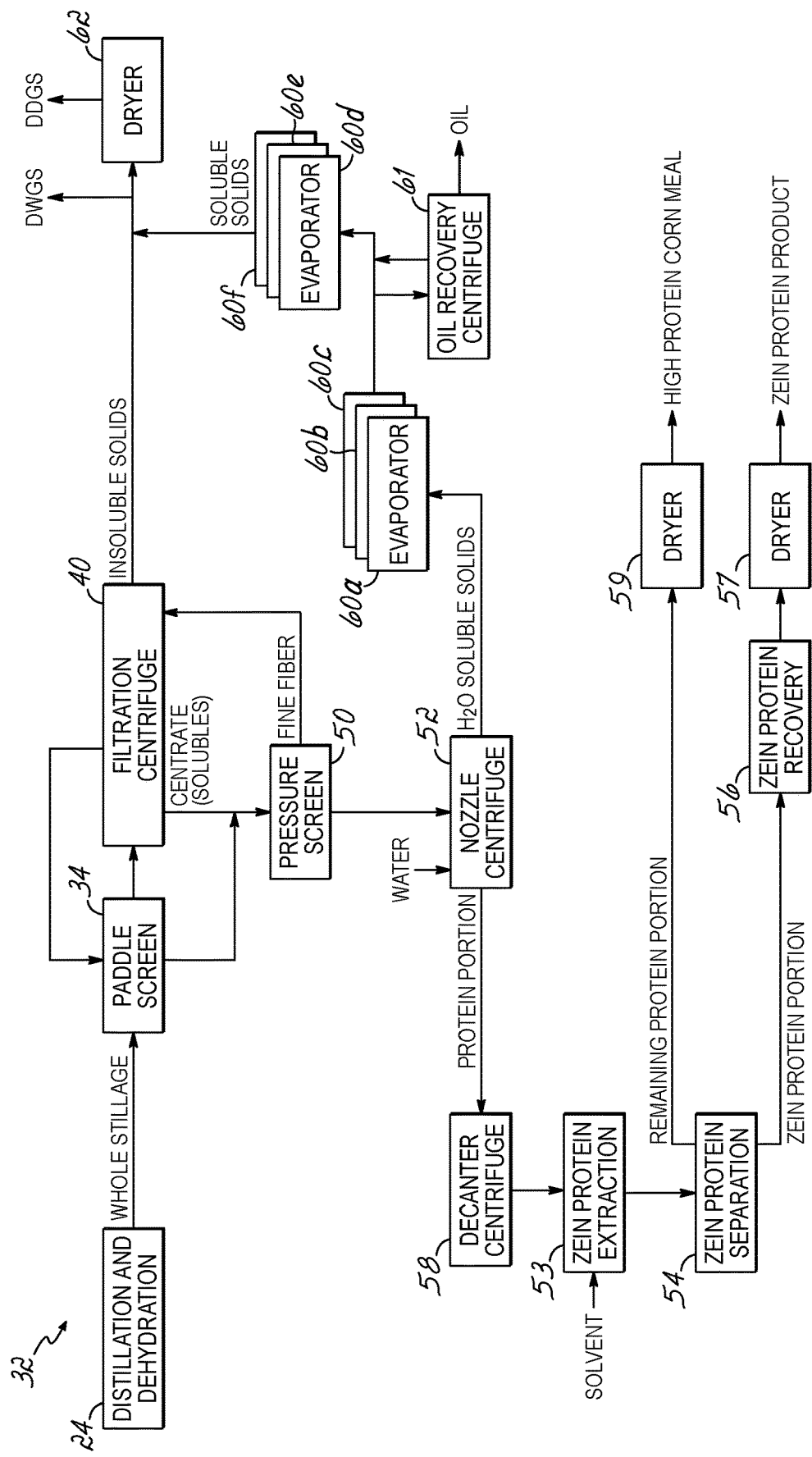
FIG. 2B is a flow diagram of a method and system for producing a zein protein product from a whole stillage byproduct produced via a corn dry-milling process for making alcohol (e.g., ethanol) in accordance with another embodiment of the invention.
Figure 2C:
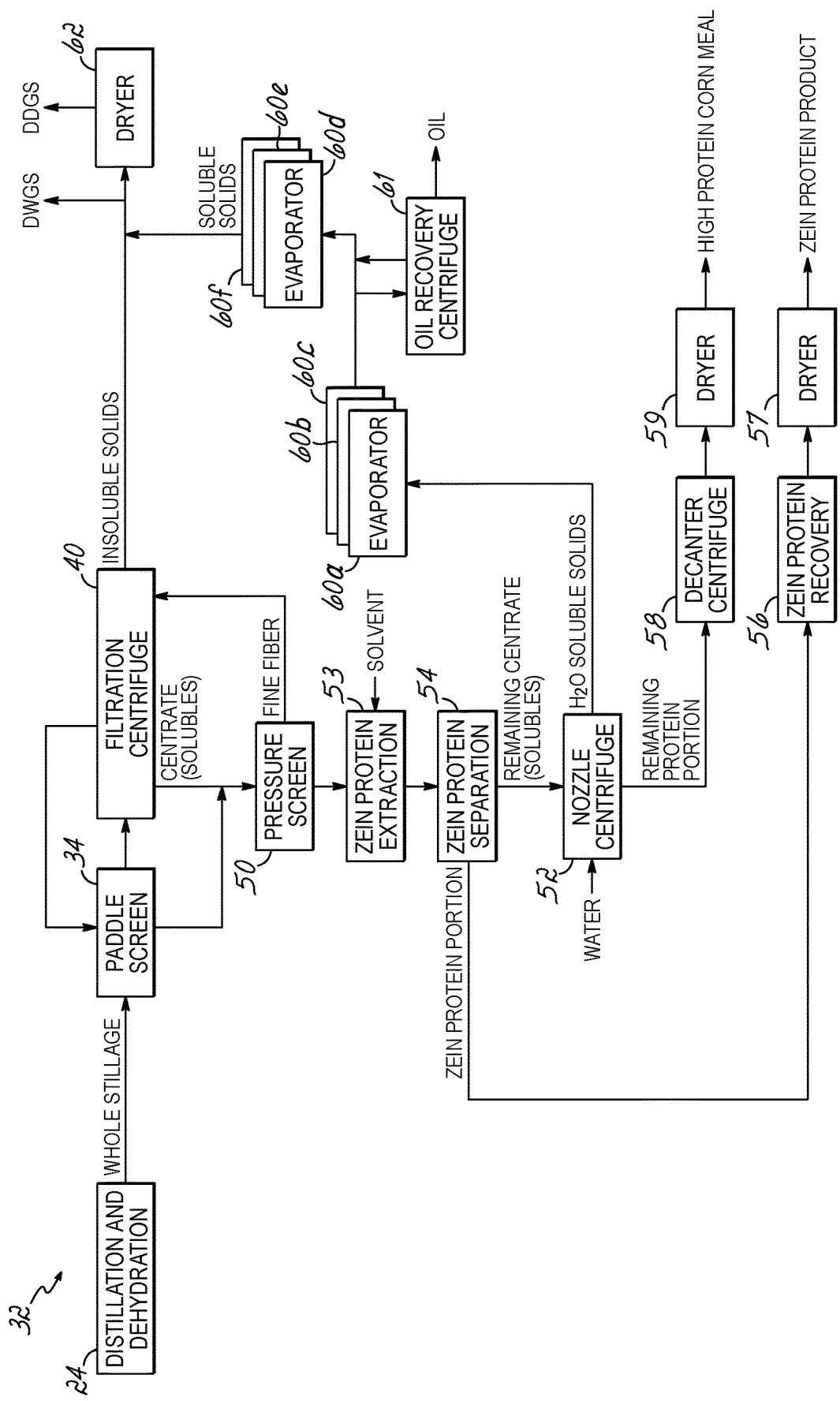
FIG. 2C is a flow diagram of a method and system for producing a zein protein product from a whole stillage byproduct produced via a corn dry-milling process for making alcohol (e.g., ethanol) in accordance with another embodiment of the invention.

In accordance with the present invention, FIGS. 2-2C schematically illustrate embodiments of a method and system, collectively numeral 32, for producing a zein protein product from the whole stillage byproduct produced in a typical corn dry-milling process 10, like that just described in FIG. 1. While a typical whole stillage byproduct is utilized here, it should be understood that the whole stillage from any corn or similar carbohydrate-containing grain dry-milling process may be utilized with the same or similar results. Again, the whole stillage byproduct contains a slurry of soluble and insoluble solids, i.e., the spent grains from the distillation and dehydration step 24, which can include protein, such as zein protein, amino acids, fiber, and oil, for example, that can be processed in accordance with embodiments of this invention to separate out the zein protein. The separated zein protein may be further processed to be sold as a zein protein product and/or used as or in, for example, coatings, fibers, adhesives, ceramics, inks, cosmetics, textiles, food products, pharmaceuticals, and biodegradable plastics.

With reference now to FIG. 2, the whole stillage byproduct can be piped from the typical corn dry-milling distillation and dehydration step 24 and subjected to an optional paddle screen 34. The optional paddle screen 34 is situated before a filtration centrifuge 40, which is further discussed below, so as to aid ultimately in separation of the insoluble solids portion, e.g., fiber, from the centrate (solubles) portion by initially filtering out desirable amounts of water, amino acids, protein, including zein protein, and, incidentally, small fiber fines from the whole stillage byproduct. This initial screening can help reduce the resulting load on the subsequent filtration centrifuge 40 or similar device. The resulting throughs (centrate) from the paddle screen 34 eventually joins with the centrate (solubles) underflow from the filtration centrifuge 40 or similar device, as will be discussed in greater detail below.

To filter the whole stillage byproduct, the optional paddle screen 34 can include screen openings of no greater than about 1000 microns. In another example, the paddle screen 34 can include openings therein of no greater than about 500 microns. In another example, the paddle screen 34 can include openings therein of no greater than about 250 microns. In yet another example, the openings therein are no greater than about 150 microns. In yet another example, the openings therein are no greater than about 75 microns. It should be understood that these values are exemplary and that those of ordinary skill in the art will recognize how to determine the size of the openings to achieve the desired filtration rates. In one example, the optional paddle screen 34 is a standard type paddle screen as is known in the art. One such suitable paddle screen 34 is the FQ-PS32 available from Fluid-Quip, Inc. of Springfield, Ohio. It should be understood that the optional paddle screen 34 may be replaced with other types of pre-concentration devices, e.g., a standard pressure screen, conic centrifuge, cyclone, or hydroclone, which can perform the desired filtration or preconcentration function. One such suitable pressure screen is the PS-Triple available from Fluid-Quip, Inc. of Springfield, Ohio. In addition, although a single paddle screen 34 is depicted, it should be understood that a plurality of paddle screens 34 or the like may be situated in-line and utilized for filtering the whole stillage byproduct.

The whole stillage from the distillation and dehydration step 24, if the optional paddle screen 34 is not present, or the cake (solids) from the optional paddle screen 34 is sent to the filtration centrifuge 40 whereat the whole stillage byproduct or overflow is separated into the insoluble solids portion, which includes fiber, and the centrate (solubles) portion, which includes protein, such as zein protein, amino acids, oil, yeast, etc. One such suitable filtration centrifuge is described in Lee et al., U.S. Pat. No. 8,813,973 entitled "Apparatus and Method for Filtering a Material from a Liquid Medium", the contents of which are expressly incorporated by reference herein in its entirety. The filtration centrifuge 40 may be configured to perform both the initial filtering (sometimes referred to as a pre-concentration) of the whole stillage byproduct and washing of the fiber so as to clean the fiber and remove the protein, including zein protein, amino acids, oil, yeast, and other components that remain associated with the fiber after the initial filtration or pre-concentration.

With respect to the filtration centrifuge 40, the washing of the fiber may include a washing cycle, wherein the fiber is mixed and rinsed in wash water, followed by a de-watering cycle, wherein the wash water is separated from the fiber. The washing of the fiber may include multiple rinsing/de-watering cycles. Additionally, a counter current washing technique may be employed to save wash water usage. After washing the fiber, but before the fiber exits the centrifuge, the fiber may go through an enhanced de-watering stage, a compaction stage, and/or an air dry stage to further de-water or dry the fiber. This may reduce the dryer capacity or eliminate the dryer altogether. Eventually, the washed and filtered fiber exits the filtration centrifuge 40 so that the fiber can be further processed, as discussed further below to result in a desired product, such as DWGS or DDGS. In one example, the fiber can be transported to a remote site for further processing. Moreover, any separated out portion of slurry from the fiber, e.g., water, protein, amino acids, oil, etc., which occurs via screening, is collected to define the centrate (solubles) stream, then transported and further processed as described below. Optionally, a portion of the slurry and/or wash water may be piped back to the optional paddle screen 34 for further reprocessing. The filtration centrifuge 40 may provide the filtered material at a water concentration of between about 55% and about 75% water, which is a significant reduction compared to conventional filtration systems.

With continuing reference to FIG. 2, although a single filtration centrifuge 40 is depicted, it should be understood that a plurality of filtration centrifuges 40 may be situated in-line and utilized for separating the whole stillage byproduct into its insoluble solids portion (fiber) and centrate (solubles) portion. In an alternate embodiment, it is contemplated that the filtration centrifuge 40 can be replaced by a standard pressure screen, decanter centrifuge, a paddle screen, or other like devices as are known in the art to separate the whole stillage byproduct into the insoluble solids portion and centrate (solubles) portion. One such suitable pressure screen is the PS-Triple available from Fluid-Quip, Inc. of Springfield, Ohio. One such suitable decanter centrifuge is the NX-944HS available from Alfa Laval of Lund, Sweden. One such suitable paddle screen is the FQ-PS32 available from Fluid-Quip, Inc. of Springfield, Ohio.

As further shown in FIG. 2, the centrate (solubles) underflow from the filtration centrifuge 40 is piped to join up with the centrate from the optional paddle screen 34 prior to or at an optional standard pressure screen 50, as is known in the art, to further aid in separation of any fine fiber from the centrate (solubles) portion. If the optional paddle screen 34 is not present, the centrate (solubles) underflow from the filtration centrifuge 40 is sent directly to optional pressure screen 50. Prior to being subjected to the optional pressure screen 50, the protein content within this stream, which includes zein protein, ranges from 21.2% to 33.4% and solids content within this stream ranges from 8.7% to 10.9%. Other ranges are contemplated and achievable based on processing conditions.

Fiber having a size less than that of the screen of the filtration centrifuge 40 and/or optional paddle screen 34 may pass through and to subsequent steps of the corn dry-milling process. At the pressure screen 50, the separated fine fiber can be separated from the centrate (solubles) and piped back to the filtration centrifuge 40 or similar unit operations whereat the fine fiber may be filtered out. One such suitable pressure screen 50 is the PS-Triple available from Fluid-Quip, Inc. of Springfield, Ohio. In an alternate embodiment, the optional pressure screen 50 may be replaced with a standard paddle screen or decanter centrifuge, as are mentioned above, or other like device, to aid in separation of the fine fiber from the centrate (solubles) portion. In addition, although a single pressure screen 50 is depicted, it should be understood that a plurality of pressure screens 50 may be situated in-line and utilized for filtering the centrate (solubles) underflow.

The remaining centrate (solubles) portion from the optional pressure screen 50 is piped and subjected to a nozzle centrifuge 52. Alternatively, if the optional pressure screen 50 is not present, the centrate (solubles) can be sent directly to the nozzle centrifuge 52. The nozzle centrifuge 52 can be provided with washing capabilities so that fresh water, along with the centrate (solubles) portion, can be supplied to the nozzle centrifuge 52. The additional fresh water allows for easier separation of the centrate (solubles) into its protein portion and water soluble solids portion. The nozzle centrifuge 52 separates the centrate (solubles) into a protein portion, which includes zein protein, and a water soluble solids portion. The heavier protein portion separates from the water soluble solids portion and is removed as the underflow whereas the lighter water soluble solids portion, which includes oil and sugars, can be removed as the overflow. One such suitable nozzle centrifuge 52 is the FQC-950 available from Fluid-Quip, Inc. of Springfield, Ohio. In an alternate embodiment, the nozzle centrifuge 52 can be replaced with a standard cyclone apparatus or other like device, as are known in the art, to separate the centrate (solubles) portion into the underflow protein portion and overflow water soluble solids portion. One such suitable cyclone apparatus is the RM-12-688 available from Fluid-Quip, Inc. of Springfield, Ohio. It is contemplated that other suitable apparatuses may be utilized here, which may effectively separate the components by other than weight, for example. The resulting protein portion from the nozzle centrifuge 52 can then be piped and subjected to a zein protein extraction step 53.

At the zein protein extraction step 53, the zein protein in the protein portion can be separated therefrom by extraction using a suitable solvent that solubilizes the zein protein. In one example, a polar solvent such as an aqueous solution of an alcohol, e.g., ethanol or isopropanol, can be added to the protein portion to solubilize the zein protein and extract it therefrom. Zein protein is not generally soluble in water except in the presence of an alcohol solvent or, for example, high concentrations of urea or alkali (pH 11 or above), or anionic detergents. Other alcohols suitable for use include, for example, methanol, isobutanol, and propyl alcohol. In one example, the aqueous alcohol solution is 20-99% alcohol. In another example, the aqueous alcohol solution is 30-95% alcohol. In another example, the aqueous alcohol solution is 40-90% alcohol. In another example, the aqueous alcohol solution is 50-90% alcohol. Other suitable solvents can include an anhydrous alcohol solution (e.g., methanol), ketones (e.g., methyl ethyl ketone and acetone), amide solvents (e.g., acetamide), high concentrations of salts (e.g., NaCl or KBr solutions), esters, and glycols. Mixtures and combinations of suitable solvents may also be used for extraction. Heat and/or one or more reducing agents may be added to aid in solubilizing the zein protein.

After the zein extraction step, the protein portion with its solubilized zein protein can be subjected to a zein protein separation step 54 to separate the extracted zein protein from the remaining protein. Separation can be accomplished using, for example, filtration, such as micro and/or ultrafiltration, and/or centrifugation. Concerning microfiltration devices, microfiltration membranes typically include polymer, ceramic, paper, or metal membrane disc or pleated cartridge filters generally rated in the 0.1 to 2 micron range and that generally operate in the 1 to 25 psig pressure range. One such suitable microfiltration separator is the PURON PLUS MBS system provided by Koch Membrane Systems of Wichita, Kans. Ultrafiltration is a crossflow process generally rated in the 10 angstrom to 0.1 micron range and that generally operates in the 10 to 100 psig range. One such suitable ultrafiltration separator is the HFK Series Ultrafiltration provided by Koch Membrane Systems of Wichita, Kans. Centrifugation can be accomplished by means and methods known in the art. In one example, a decanter or filtration centrifuge can be used. In addition, although a single zein protein extraction step 53 and a zein protein separation step 54 are depicted, it should be understood that a plurality of zein protein extraction steps 53 and/or separation steps 54 may occur in-line, either in series or parallel, and utilized for extracting and/or separating the zein protein portion. And although not specifically shown, the filtrate or separated zein protein portion from the zein protein separation step 54 may be further clarified by standing or vacuum filtration methods and/or may be further subjected to a non-solvent, such as toluol, toluene, hexane, or benzene, for removal of non-protein impurities, such as fats and color pigments.

The zein in the resulting zein protein portion from the zein protein separation step 54 can be recovered at zein protein recovery step 56 by means and methods known in the art, such as by precipitation thereof using excess amounts of cold water and/or low temperature (e.g., 0 to −25° C.), solvent removal methods, and the like. Thereafter, the recovered zein protein product can be further optionally dried, such as by being sent to a vacuum dryer 57, as is known in the art, or via other drying methods. In one embodiment, the final dried zein protein product includes at least 30 wt % zein protein on a dry basis. In another embodiment, the final dried zein protein product includes at least 80 wt % zein protein on a dry basis. The final dried zein protein product may be further processed to be sold and/or used as or in, for example, coatings, fibers, adhesives, ceramics, inks, cosmetics, textiles, food products, pharmaceutical, and biodegradable plastics.

The filtered out and remaining protein portion from the zein protein separation step 54 can be subjected to a decanter centrifuge 58. At the decanter centrifuge 58, the remaining protein portion can be dewatered to provide a dewatered remaining protein portion. The decanter centrifuge 58 is standard and known in the art. One such suitable decanter centrifuge 58 is the NX-944HS available from Alfa Laval of Lund, Sweden. In addition, although a single decanter centrifuge 58 is depicted, it should be understood that a plurality of decanter centrifuges 58 may be situated in-line, either in series or parallel. In an alternate embodiment, the decanter centrifuge 58 may be replaced with a standard filter press or rotary vacuum, or other like device, as are known in the art, to dewater the protein portion. A water portion or filtrate from the decanter centrifuge 58 may be recycled back, for example, to liquefaction step 16 or fermentation step 20 for reuse in the dry-milling process.

The dewatered protein portion can be further optionally dried, such as by being sent to a dryer 59, e.g., a spray dryer, as is known in the art. In another embodiment, the remaining protein portion can be subjected to vacuum filtration or other drying methods, as are known in the art. The final dried protein product defines a high protein corn meal. In one example, the final dried protein product defines a high protein corn meal that includes, for example, at least 35 wt % protein on a dry basis and which may be sold as pig, ruminant, fish, or chicken feed, for example. In another embodiment, the final dried protein product defines a high protein corn meal that includes, for example, at least 40 wt % protein on a dry basis and which may be sold as pig, ruminant, fish, or chicken feed, for example. In another embodiment, the high protein corn meal includes at least 45 wt % protein on a dry basis. In another embodiment, the high protein corn meal includes at least 50 wt % protein on a dry basis. In yet another embodiment, the high protein corn meal includes at least 60 wt % protein on a dry basis. In still another embodiment, the high protein corn meal includes about 56 wt % protein on a dry basis. The resulting high protein corn meal may be sold at a much higher cost per ton than DDGS or DWGS. It should be understood that the type and concentration of protein in the zein protein product and high protein corn meal may vary based on the carbohydrate-containing grain source, the fermentation process, and/or the specific application.

Returning now to the separated water soluble solids portion or filtrate from the nozzle centrifuge 52, which includes oil as well as minerals and soluble proteins, the separated water soluble solids portion may be recycled back, for example, to the liquefaction step 16 or the fermentation step 20 for reuse in the dry-milling process. Additionally or alternatively, as shown in FIG. 2, the water soluble solids portion can be piped from the nozzle centrifuge 52 and subjected to a set of three evaporators 60a, 60b, and 60c, as are known in the art, to begin separating the soluble solids from the water soluble solids portion. The evaporators 60a-c evaporate the liquid portion of the water soluble solids portion. Thereafter, the water soluble solids portion can be piped and subjected to an optional oil recovery centrifuge 61, as is known in the art, so that oil can be removed therefrom. One such suitable oil recovery centrifuge 261 is the ORPX 617 available from Alfa Laval of Lund, Sweden. In one example, the final recovered oil product can include between about 40 wt % to about 60 wt % of the total corn oil in the corn. In comparison to typical oil recovery in a standard dry-milling process, oil recovery centrifuge 61 can function at a higher capacity because the water soluble solids portion, which is subjected to the oil recovery centrifuge 61, includes less liquid and less protein and fiber than normal.

The remainder of the water soluble solids portion can be piped and subjected to another set of three evaporators 60d, 60e, and 60f whereat the liquid portion is further evaporated from the water soluble solids portion to ultimately yield a soluble solids portion. While the water soluble solids portion is subjected to two sets of three evaporators 60a-c, 60d-f, it should be understood that the number of evaporators and sets thereof can be varied, i.e., can be more or less, from that shown depending on the particular application and result desired.

The resulting soluble solids portion may be combined with the insoluble solids portion, e.g., fiber, received from the filtration centrifuge 40 to provide distillers wet grains with soluble (DWGS), which may be further dried by a dryer 62, as is known in the art, to provide distillers dry grains with solubles (DDGS), both of which can be sold to dairy and beef feedlots. In another example, the soluble solids portion may be used as a natural fertilizer. In another example, the soluble solids portion may be used as a raw material feed source for conversion to simple sugar, which than can be further converted to bioethanol or other biochemical processes.

Accordingly, in this dry-milling process, neither the DDGS nor DWGS receive the typical concentrated syrup from the evaporators 60. Despite the lower protein content, the DDGS and DWGS may still be sold to beef and dairy feedlots as cattle feed or other animal feed markets.

While the method and system 32 of FIG. 2 herein focuses on separating a zein protein portion from a stream coming directly from the nozzle centrifuge 52, it should be understood that other locations in the method and system 32 may be considered and exploited for separating zein protein, if so desired. In one example, as shown in FIG. 2B, a zein protein portion may be separated from a dewatered protein portion after the decanter centrifuge 58. In this manner, the protein portion stream coming from the nozzle centrifuge 52 is first subjected to decanter centrifuge 58, then the dewatered protein portion is subjected to the zein protein extraction step 53, followed by zein protein separation 54 to provide a zein protein portion and the remaining protein portion. Thereafter, the remaining protein portion from the zein protein separation step 54 can be optionally subjected to dryer 59, and the zein protein product can be recovered at zein protein recovery step 56 then optionally dried to provide a zein product.

In yet another embodiment, as shown in FIG. 2C, a zein protein portion may be separated from the stream, or centrate (solubles) portion, intended for the nozzle centrifuge, including, for example, the stream directly after the optional pressure screen 50. In this manner, the centrate (solubles) stream coming from the optional pressure screen 50 or filtration centrifuge 40 is first subjected to the zein protein extraction step 53, followed by zein protein separation 54 to provide a zein protein portion and remaining centrate (solubles) stream. The zein protein portion can be recovered at zein protein recovery step 56 then optionally dried to provide a zein product. And the remaining centrate (solubles) stream from the zein protein separation step 54 is subjected to the nozzle centrifuge whereat the water soluble solids portion can be separated from the remaining protein portion. The remaining protein portion can be subjected to the decanter centrifuge 58 optionally followed by dryer 59, and the water soluble solids portion is further treated as discussed above.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the scope of applicant's general inventive concept.

What is claimed is:

1. A method for producing a zein protein product from a whole stillage byproduct, the method comprising:
   filtering a whole stillage byproduct, via particle sizes, into an insoluble solids portion, which includes fiber for producing distiller's grains, and a centrate portion, which includes zein protein, wherein the whole stillage byproduct is not combined with alcohol prior to filtering the whole stillage byproduct and the separated centrate portion remains separate from the insoluble solids portion;
   thereafter, separating the separated centrate portion, via weights, into a protein portion including the zein protein, and a water soluble solids portion, wherein the protein portion including the zein protein is not subsequently subjected to an evaporator;
   thereafter, separating the zein protein from the separated protein portion to define a zein protein portion and a remaining protein portion;
   recovering the zein protein portion to define a zein protein product; and obtaining a zein protein product with at least 30 wt % zein protein on a dry basis.

2. The method of claim 1 wherein separating the whole stillage byproduct, via particle sizes, into an insoluble solids portion, which includes fiber for producing distiller's grains, and a separate centrate portion includes subjecting the whole stillage byproduct to a filtration centrifuge, a pressure screen, or a paddle screen to separate the whole stillage byproduct, via particle sizes, into the insoluble solids portion and the centrate portion.

3. The method of claim 1 wherein separating the separated centrate portion, via weights, includes subjecting the separated solubles portion to a nozzle centrifuge or cyclone apparatus to separate, via weights, the separated solubles portion into a protein portion including the zein protein, and a water soluble solids portion.

4. The method of claim 1 wherein separating the zein protein from the protein portion includes extracting the zein protein from the protein portion, then separating the extracted zein protein from the protein portion to define the zein protein portion.

5. The method of claim 4 wherein extracting the zein protein from the protein portion includes extracting the zein protein from the protein portion via a solvent, then separating the extracted zein protein from the protein portion to define the zein protein portion.

6. The method of claim 1 wherein separating the zein protein from the protein portion includes filtering and/or centrifuging out the zein protein from the protein portion to define the zein protein portion.

7. The method of claim 1 wherein recovering the zein protein portion to define the zein protein product includes precipitating out or removing solvent from the zein portion to define the zein protein product.

8. The method of claim 1 further comprising drying the recovered zein portion to define the zein protein product, which includes at least 30 wt % zein protein on a dry basis.

9. The method of claim 1 further comprising, after separating the zein protein from the protein portion, recovering the remaining protein portion to define a high protein corn meal that includes at least 35 wt % protein on a dry basis.

10. The method of claim 1 further comprising separating out water from the water soluble solids portion to yield a soluble solids portion.

11. The method of claim 10 further comprising combining the soluble solids portion with the insoluble solids portion, which includes fiber, to provide distillers wet or dry grains with solubles.

12. The method of claim 1 further comprising separating oil from the water soluble solids portion to provide an oil portion.

13. The method of claim 1 wherein the zein protein product includes at least 80 wt % zein protein on a dry basis.

14. A method for producing a zein protein product from a whole stillage byproduct, the method comprising:
   filtering a whole stillage byproduct, via particle sizes, into an insoluble solids, which includes fiber for producing distiller's grains, and a separate centrate portion, which includes zein protein, wherein the whole stillage byproduct is not combined with alcohol prior to filtering the whole stillage byproduct and the separated centrate portion remains separate from the insoluble solids portion;
   thereafter, separating the separated centrate portion, via weights, into a protein portion including the zein protein, and a water soluble solids portion, wherein the protein portion including the zein protein is not subsequently subjected to an evaporator;
   thereafter, extracting the zein protein from the protein portion, then separating the extracted zein protein from the protein portion to define a zein protein portion and a remaining protein portion;
   precipitating out the zein protein portion or removing solvent from the zein protein portion to define a zein protein product; and obtaining a zein protein product with at least 30 wt % zein protein on a dry basis.

15. The method of claim 14 wherein separating the extracted zein protein from the protein portion includes filtering and/or centrifuging out the extracted zein protein from the protein portion to define the zein protein portion.

16. The method of claim 14 further comprising after precipitating out the zein protein portion or removing solvent from the zein protein portion, drying the zein protein portion to define the zein protein product, which includes at least 30 wt % zein protein on a dry basis.

17. The method of claim 14 wherein extracting the zein protein from the protein portion includes extracting the zein protein from the protein portion via a solvent, then separating the extracted zein protein from the protein portion to define the zein protein portion and the remaining protein portion.

18. The method of claim 14 wherein the zein protein product includes at least 80 wt % zein protein on a dry basis.

19. The method of claim 14 wherein filtering the whole stillage byproduct, via particle sizes, into an insoluble solids portion, which includes fiber for producing distiller's grains, and a separate centrate portion includes subjecting the whole stillage byproduct to a filtration centrifuge, a pressure screen, or a paddle screen to filter the whole stillage byproduct, via particle sizes, into the insoluble solids portion, which includes fiber for producing distiller's grains, and the separate centrate portion, and wherein, prior to evaporation, separating the separated centrate portion includes subjecting the separated centrate portion to a nozzle centrifuge or cyclone apparatus to separate the separated centrate portion into the protein portion including the zein protein, and the water soluble solids portion.

* * * * *